United States Patent
Greff

(10) Patent No.: US 8,821,918 B2
(45) Date of Patent: *Sep. 2, 2014

(54) CROSS-LINKED GELATIN COMPOSITION COMPRISING A WETTING AGENT

(71) Applicant: Boston Scientific Scimed, Inc., Maple Grove, MN (US)

(72) Inventor: Richard J. Greff, St. Pete Beach, FL (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,472

(22) Filed: Aug. 15, 2013

(65) Prior Publication Data

US 2013/0324470 A1 Dec. 5, 2013

Related U.S. Application Data

(63) Continuation of application No. 13/477,541, filed on May 22, 2012, now Pat. No. 8,524,270, which is a continuation of application No. 10/068,812, filed on Feb. 4, 2002, now Pat. No. 8,187,625.

(60) Provisional application No. 60/275,420, filed on Mar. 12, 2001.

(51) Int. Cl.
| | |
|---|---|
| A61F 13/00 | (2006.01) |
| A61K 9/70 | (2006.01) |
| A61L 15/16 | (2006.01) |
| A61L 15/00 | (2006.01) |
| A61L 26/00 | (2006.01) |
| A61K 47/10 | (2006.01) |
| A61K 47/20 | (2006.01) |
| A61K 47/32 | (2006.01) |
| A61K 47/34 | (2006.01) |
| A61K 47/26 | (2006.01) |
| A61K 38/00 | (2006.01) |

(52) U.S. Cl.
CPC .............. *A61K 47/34* (2013.01); *A61L 26/0038* (2013.01); *A61K 47/10* (2013.01); *A61L 26/0085* (2013.01); *A61K 47/20* (2013.01); *A61K 47/32* (2013.01); *A61K 38/00* (2013.01); *A61K 47/26* (2013.01); *A61L 26/009* (2013.01); *A61L 2400/04* (2013.01)
USPC ........... 424/443; 424/444; 424/445; 424/446; 424/447

(58) Field of Classification Search
None
See application file for complete search history.

(56) References Cited

U.S. PATENT DOCUMENTS

| | | |
|---|---|---|
| 581,235 A | 4/1897 | Kenyon |
| 1,578,517 A | 3/1926 | Hein |

(Continued)

FOREIGN PATENT DOCUMENTS

| | | |
|---|---|---|
| EP | 0476178 A1 | 3/1992 |
| EP | 0482350 A2 | 4/1992 |

(Continued)

OTHER PUBLICATIONS

Correll, et al., Surg. Gyn. and Obst., 82:585 (1945).*

(Continued)

*Primary Examiner* — Isis Ghali
(74) *Attorney, Agent, or Firm* — Seager, Tufte & Wickhem LLC

(57) ABSTRACT

Disclosed is a biocompatible, hemostatic, cross-linked gelatin composition comprising a biocompatible material comprising cross-linked gelatin and a sufficient amount of wetting agent to permit uniform wetting of the sponge in the presence of an aqueous solution.

6 Claims, 1 Drawing Sheet

(56) References Cited

U.S. PATENT DOCUMENTS

| | | | |
|---|---|---|---|
| 2,086,580 A | 7/1937 | Shirley | |
| 2,370,319 A | 2/1945 | Lippincott | |
| 2,465,357 A | 3/1949 | Correll | |
| 2,492,458 A | 12/1949 | Bering, Jr. | |
| 2,507,244 A | 5/1950 | Correll et al. | |
| 2,558,395 A | 6/1951 | Studer | |
| 2,597,011 A | 5/1952 | MacMasters et al. | |
| 2,680,442 A | 6/1954 | Linzmayer | |
| 2,761,446 A | 9/1956 | Reed | |
| 2,814,294 A | 11/1957 | Figge | |
| 2,824,092 A | 2/1958 | Thompson | |
| 2,874,776 A | 2/1959 | Hooe | |
| 2,899,362 A | 8/1959 | Sieger et al. | |
| 2,997,195 A | 8/1961 | Yat Chuen Yuen | |
| 3,157,524 A | 11/1964 | Artandi | |
| 3,325,366 A * | 6/1967 | Henderson et al. | 424/78.25 |
| 3,358,689 A | 12/1967 | Higgins | |
| 3,411,505 A | 11/1968 | Nobis | |
| 3,703,174 A | 11/1972 | Smith | |
| 3,724,465 A | 4/1973 | Duchane | |
| 3,736,939 A | 6/1973 | Taylor | |
| 4,000,741 A | 1/1977 | Binard et al. | |
| 4,098,728 A | 7/1978 | Rosenblatt | |
| 4,211,323 A | 7/1980 | Olsen | |
| 4,218,155 A | 8/1980 | Weidner | |
| 4,219,026 A | 8/1980 | Layton | |
| 4,224,945 A | 9/1980 | Cohen | |
| 4,238,480 A | 12/1980 | Sawyer | |
| 4,292,972 A * | 10/1981 | Pawelchak et al. | 604/368 |
| 4,323,072 A | 4/1982 | Rosenbluth et al. | |
| 4,340,066 A | 7/1982 | Shah | |
| 4,390,018 A | 6/1983 | Zukowski | |
| 4,404,970 A | 9/1983 | Sawyer | |
| 4,405,314 A | 9/1983 | Cope | |
| 4,515,637 A | 5/1985 | Cioca | |
| 4,573,576 A | 3/1986 | Krol | |
| 4,587,969 A | 5/1986 | Gillis | |
| 4,588,395 A | 5/1986 | Lemelson | |
| 4,591,094 A | 5/1986 | Morris | |
| 4,619,261 A | 10/1986 | Guerriero | |
| 4,619,913 A | 10/1986 | Luck et al. | |
| 4,644,649 A | 2/1987 | Seaman | |
| 4,645,488 A | 2/1987 | Matukas | |
| 4,696,812 A * | 9/1987 | Silbering et al. | 424/445 |
| 4,699,616 A | 10/1987 | Nowak | |
| 4,708,718 A | 11/1987 | Daniels | |
| 4,744,364 A | 5/1988 | Kensey | |
| 4,790,819 A | 12/1988 | Li et al. | |
| 4,829,994 A | 5/1989 | Kurth | |
| 4,832,688 A | 5/1989 | Sagae et al. | |
| 4,836,204 A | 6/1989 | Landymore et al. | |
| 4,839,204 A | 6/1989 | Yoshino | |
| 4,850,960 A | 7/1989 | Grayzel | |
| 4,852,568 A | 8/1989 | Kensey | |
| 4,869,143 A | 9/1989 | Merrick et al. | |
| 4,890,612 A | 1/1990 | Kensey | |
| 4,900,303 A | 2/1990 | Lemelson | |
| 4,920,158 A | 4/1990 | Murray et al. | |
| 4,929,246 A | 5/1990 | Sinofsky | |
| 4,936,835 A | 6/1990 | Haaga | |
| 4,950,234 A | 8/1990 | Fujioka et al. | |
| 5,007,895 A | 4/1991 | Burnett | |
| 5,021,059 A | 6/1991 | Kensey et al. | |
| 5,049,138 A | 9/1991 | Chevalier et al. | |
| 5,053,046 A | 10/1991 | Janese | |
| 5,061,274 A | 10/1991 | Kensey | |
| 5,080,655 A | 1/1992 | Haaga | |
| 5,106,376 A | 4/1992 | Mononen et al. | |
| 5,108,421 A | 4/1992 | Fowler | |
| 5,129,889 A | 7/1992 | Hahn | |
| 5,160,323 A | 11/1992 | Andrew | |
| 5,163,904 A | 11/1992 | Lampropoulos et al. | |
| 5,167,624 A | 12/1992 | Butler et al. | |
| 5,192,290 A | 3/1993 | Hilal | |
| 5,192,300 A | 3/1993 | Fowler | |
| 5,192,301 A | 3/1993 | Kamiya et al. | |
| 5,195,988 A | 3/1993 | Haaga | |
| 5,219,899 A | 6/1993 | Panster et al. | |
| 5,220,926 A | 6/1993 | Jones | |
| 5,221,259 A | 6/1993 | Weldon et al. | |
| 5,232,453 A | 8/1993 | Plass et al. | |
| 5,242,683 A | 9/1993 | Klaveness | |
| 5,254,105 A | 10/1993 | Haaga | |
| 5,275,616 A | 1/1994 | Fowler | |
| 5,282,827 A | 2/1994 | Kensey et al. | |
| 5,299,581 A | 4/1994 | Donnell et al. | |
| 5,310,407 A | 5/1994 | Casale | |
| 5,320,639 A | 6/1994 | Rudnick | |
| 5,322,515 A | 6/1994 | Karas et al. | |
| 5,325,857 A | 7/1994 | Nabai et al. | |
| 5,334,216 A | 8/1994 | Vidal et al. | |
| 5,342,388 A | 8/1994 | Toller | |
| 5,350,399 A | 9/1994 | Erlebacher et al. | |
| 5,352,211 A | 10/1994 | Merskelly | |
| 5,366,480 A | 11/1994 | Corriveau et al. | |
| 5,370,656 A | 12/1994 | Shevel | |
| 5,383,896 A | 1/1995 | Gershony et al. | |
| 5,383,899 A | 1/1995 | Hammerslag | |
| 5,385,550 A | 1/1995 | Su et al. | |
| 5,388,588 A | 2/1995 | Nabai et al. | |
| 5,391,183 A | 2/1995 | Janzen et al. | |
| 5,399,361 A | 3/1995 | Song et al. | |
| 5,417,699 A | 5/1995 | Klein | |
| 5,419,765 A | 5/1995 | Weldon et al. | |
| 5,431,639 A | 7/1995 | Shaw | |
| 5,437,292 A | 8/1995 | Kipshidze et al. | |
| 5,437,631 A | 8/1995 | Janzen | |
| 5,443,481 A | 8/1995 | Lee | |
| 5,447,502 A | 9/1995 | Haaga | |
| 5,458,570 A | 10/1995 | May, Jr. | |
| 5,462,194 A | 10/1995 | Barnwell | |
| 5,467,780 A | 11/1995 | Nabai et al. | |
| 5,478,352 A | 12/1995 | Fowler | |
| 5,479,936 A | 1/1996 | Nabai et al. | |
| 5,486,195 A | 1/1996 | Myers et al. | |
| 5,490,736 A | 2/1996 | Haber | |
| 5,507,279 A | 4/1996 | Fortune | |
| 5,522,840 A | 6/1996 | Krajicek | |
| 5,522,850 A | 6/1996 | Yomtov et al. | |
| 5,526,822 A | 6/1996 | Burbank et al. | |
| 5,527,332 A | 6/1996 | Clement | |
| 5,529,577 A | 6/1996 | Hammerslag | |
| 5,540,715 A | 7/1996 | Katsaros et al. | |
| 5,542,914 A | 8/1996 | Van Iten | |
| 5,545,175 A | 8/1996 | Abidin et al. | |
| 5,545,178 A | 8/1996 | Kensey et al. | |
| 5,554,108 A | 9/1996 | Browning et al. | |
| 5,558,853 A | 9/1996 | Quay | |
| 5,571,168 A | 11/1996 | Toro | |
| 5,591,204 A | 1/1997 | Janzen et al. | |
| 5,591,205 A | 1/1997 | Fowler | |
| 5,595,735 A | 1/1997 | Saferstein et al. | |
| 5,601,207 A | 2/1997 | Paczonay | |
| 5,601,601 A | 2/1997 | Tal et al. | |
| 5,601,602 A | 2/1997 | Fowler | |
| 5,601,603 A | 2/1997 | Illi | |
| 5,620,461 A | 4/1997 | Muijs Van De Moer et al. | |
| 5,645,566 A | 7/1997 | Brenneman et al. | |
| 5,645,849 A | 7/1997 | Pruss et al. | |
| 5,649,547 A | 7/1997 | Ritchart et al. | |
| 5,653,730 A | 8/1997 | Hammerslag | |
| 5,660,854 A * | 8/1997 | Haynes et al. | 424/450 |
| 5,665,107 A | 9/1997 | Hammerslag | |
| 5,674,346 A | 10/1997 | Kundel | |
| 5,676,689 A | 10/1997 | Kensey et al. | |
| 5,681,279 A | 10/1997 | Roper et al. | |
| 5,707,393 A | 1/1998 | Kensey et al. | |
| 5,716,375 A | 2/1998 | Fowler | |
| 5,725,498 A | 3/1998 | Janzen et al. | |
| 5,741,223 A | 4/1998 | Janzen et al. | |
| 5,769,086 A | 6/1998 | Ritchart et al. | |
| 5,775,333 A | 7/1998 | Burbank et al. | |
| 5,782,861 A | 7/1998 | Cragg et al. | |
| 5,800,389 A | 9/1998 | Burney et al. | |

(56) References Cited

U.S. PATENT DOCUMENTS

| | | |
|---|---|---|
| 5,810,806 A | 9/1998 | Ritchart et al. |
| 5,827,218 A | 10/1998 | Nguyen et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,931,165 A | 8/1999 | Reich et al. |
| 5,984,950 A | 11/1999 | Cragg et al. |
| 6,007,563 A | 12/1999 | Nash et al. |
| 6,027,471 A | 2/2000 | Fallon et al. |
| 6,027,482 A | 2/2000 | Imbert |
| 6,033,427 A | 3/2000 | Lee |
| 6,056,768 A | 5/2000 | Cates et al. |
| 6,063,061 A | 5/2000 | Wallace et al. |
| 6,066,325 A | 5/2000 | Wallace et al. |
| 6,071,300 A | 6/2000 | Brenneman et al. |
| 6,071,301 A | 6/2000 | Cragg et al. |
| 6,086,607 A | 7/2000 | Cragg et al. |
| 6,090,130 A | 7/2000 | Nash et al. |
| 6,126,675 A | 10/2000 | Shchervinsky et al. |
| 6,161,034 A | 12/2000 | Burbank et al. |
| 6,162,192 A | 12/2000 | Cragg et al. |
| 6,183,497 B1 | 2/2001 | Sing et al. |
| 6,197,327 B1 | 3/2001 | Harrison et al. |
| 6,200,328 B1 | 3/2001 | Cragg et al. |
| 6,315,753 B1 | 11/2001 | Cragg et al. |
| 6,371,974 B1 | 4/2002 | Brenneman et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,503,222 B2 | 1/2003 | Lo |
| 6,527,734 B2 | 3/2003 | Cragg et al. |
| 6,540,735 B1 | 4/2003 | Ashby et al. |
| 6,544,236 B1 | 4/2003 | Cragg et al. |
| 6,547,806 B1 | 4/2003 | Ding |
| 6,585,680 B2 | 7/2003 | Bugge |
| 6,610,026 B2 | 8/2003 | Cragg et al. |
| 6,706,690 B2 | 3/2004 | Reich et al. |
| 6,846,320 B2 | 1/2005 | Ashby et al. |
| 6,863,680 B2 | 3/2005 | Ashby |
| 6,964,658 B2 | 11/2005 | Ashby et al. |
| 6,984,219 B2 | 1/2006 | Ashby et al. |
| 7,008,440 B2 | 3/2006 | Sing et al. |
| 7,025,748 B2 | 4/2006 | Ashby |
| 7,029,489 B1 | 4/2006 | Ashby et al. |
| 7,037,322 B1 | 5/2006 | Sing et al. |
| 7,037,323 B2 | 5/2006 | Sing et al. |
| 7,159,716 B2 | 1/2007 | Ashby et al. |
| 7,175,646 B2 | 2/2007 | Brenneman et al. |
| 7,201,725 B1 | 4/2007 | Cragg et al. |
| 7,335,219 B1 | 2/2008 | Ashby et al. |
| 7,455,680 B1 | 11/2008 | Ashby et al. |
| 7,611,479 B2 | 11/2009 | Cragg et al. |
| 7,621,936 B2 | 11/2009 | Cragg et al. |
| 7,625,352 B1 | 12/2009 | Ashby et al. |
| 7,695,492 B1 | 4/2010 | Ashby et al. |
| 7,753,872 B2 | 7/2010 | Cragg et al. |
| 7,955,353 B1 | 6/2011 | Ashby et al. |
| 8,187,625 B2 | 5/2012 | Greff |
| 8,317,821 B1 | 11/2012 | Ashby et al. |
| 8,524,270 B2 | 9/2013 | Greff |
| 2002/0002889 A1 | 1/2002 | Ashby et al. |
| 2002/0016612 A1 | 2/2002 | Ashby et al. |
| 2002/0038133 A1 | 3/2002 | Sing et al. |
| 2002/0042378 A1 | 4/2002 | Reich et al. |
| 2002/0062104 A1 | 5/2002 | Ashby et al. |
| 2002/0156495 A1 | 10/2002 | Brenneman et al. |
| 2003/0028140 A1 | 2/2003 | Greff et al. |
| 2003/0088269 A1 | 5/2003 | Ashby |
| 2003/0088271 A1 | 5/2003 | Cragg et al. |
| 2003/0120258 A1 | 6/2003 | Ashby et al. |
| 2003/0135237 A1 | 7/2003 | Cragg et al. |
| 2004/0019328 A1 | 1/2004 | Sing et al. |
| 2004/0019330 A1 | 1/2004 | Ashby |
| 2004/0102730 A1 | 5/2004 | Davis et al. |
| 2004/0158287 A1 | 8/2004 | Cragg et al. |
| 2004/0176723 A1 | 9/2004 | Sing et al. |

FOREIGN PATENT DOCUMENTS

| | | | |
|---|---|---|---|
| EP | 0637431 A1 | | 8/1993 |
| EP | 0557963 A1 | | 9/1993 |
| EP | 0568334 A1 | | 11/1993 |
| EP | 568334 A1 | * | 11/1993 |
| EP | 0637432 B1 | | 10/1997 |
| FR | 2641692 A1 | | 7/1990 |
| GB | 1509023 A | | 4/1978 |
| GB | 1569660 A | | 6/1980 |
| JP | 02182259 A | * | 7/1990 |
| SU | 782814 A1 | | 11/1980 |
| SU | 1088709 A1 | | 4/1984 |
| WO | 9112847 A1 | | 9/1991 |
| WO | 9402072 A1 | | 2/1994 |
| WO | 9428800 A1 | | 12/1994 |
| WO | 9528124 A2 | | 10/1995 |
| WO | 9532669 A1 | | 12/1995 |
| WO | 9532671 A1 | | 12/1995 |
| WO | 9532679 A1 | | 12/1995 |
| WO | 9608208 A1 | | 3/1996 |
| WO | 9624290 A1 | | 8/1996 |
| WO | 9709934 A1 | | 3/1997 |
| WO | 9806346 A1 | | 2/1998 |
| WO | 9938543 A | | 8/1999 |
| WO | 9966834 A1 | | 12/1999 |

OTHER PUBLICATIONS

Pharmacia & Upjohn "Gelfoam is a Standard in Hemostasis", May 1997.*

Allison et al., "Percutaneous Liver Biopsy and Track Embolization with Steel Coils", Radiology, 1998, p. 261-263, vol. 169; No. 1.

Byrne. J., "Review article: Endovascular treatments for intracranial aneurysms", The British Journal of Radiology, 1996, p. 891-899. vol. 69.

Chuang et al., "Sheath Needle for Liver Biopsy in High-Risk Patients", Radiology, 1988, p. 261-262, vol. 166.

Fandrich et al., "Small gauge gelfoam plug liver biopsy in high risk patients: Safety and diagnostic value", Australasian Radiology, 1996, p. 230-234, vol. 40.

Foran et al., "Early mobilisation after percutaneous cardiac catheterisation using collagen plug (VasoSeal) haemostasis", BRHeart, 1993, p. 424-429, vol. 69.

Gelfoam Sterile Powder: absorbable gelatin powder, Pharmacia & Upjohn, Feb. 1996.

Gelfoam Sterile Powder: absorbable gelatin powder, Pharmacia & Upjohn, Inc. , Mar. 1996.

Gelfoam Sterile Sponge, Gelfoam Sterile Powder, Gelfilm Sterile Film, Pharmacia & Upjohn, Nov. 1996, p. 1-23.

Gelfoam Sterile Sponge, Gelfoam Sterile Powder, Gelfilm Sterile Film, Pharmacia & Upjohn, Sep. 1996, p. 1-33.

Gelfoam Sterile Sponge, Gelfoam Sterile Powder, Gelfoam Sterile Film, Pharmacia & Upjohn, May 1997, p. 1-34.

Gibbs et al., "Femoral Arterial Hemostasis Using a Collagen Plug After Coronary Artery Stent Implantation", Journal of Interventional Cardiology, 1992, p. 85-88, vol. 5; No. 2.

Journal of Interventional Cardiology, Jun. 1992, vol. 5; No. 2, Futura Publishing Company, Inc., Mount Kisco, New York.

Kassell et al., "Size of Intracranial Aneurysms", Neurosurgery, 1983, p. 291-297, vol. 12; No. 3.

Kiemeneij et al., "Improved Anticoagulation Management After Palmaz Schatz Coronary Stent Implantation by Sealing the Arterial Puncture Site With a Vascular Hemostasis Device", Catheterization and Cardiovascular Diagnosis, 1993, p. 317-322, vol. 30.

Kussmaul, III et al., "Rapid Arterial Hemostasis and Decreased Access Site Complications After Cardiac Catheterization and Angioplasty: Results of a Randomized Trial of a Novel Hemostatic Device", Jun. 1995, p. 1685-1692, vol. 25. No. 7.

Phrmacia & Upjohn, "GELFOAM Is a Standard in Hemostasis,"May 1997.

(56) References Cited

OTHER PUBLICATIONS

Riley et al., "Percutaneous Liver Biopsy with Plugging of Needle Track: A Safe Method for Use in Patients with Impaired Coagulation", TheLancet, Aug. 25, 1964.
Sanborn et al., "A Multicenter Randomized Trial Comparing a Percutaneous Collagen Hemostasis Device with Conventional Manual Compression After Diagnostic Angiography and Angioplasty", Interventional Cardiology, Nov. 1, 1993, p. 1273-1279, vol. 22; No. 5.
Schievink, et al., "Intracranial Aneurysms", The New England Journal of Medicine, Jan. 2, 1997, p. 28-40, vol. 336; No. 1.
Schrader et al. "Collagen Application for Sealing of Arterial Puncture Sites in Comparison to Pressure Dressing. A Randomized Trail", Catheterization and Cardiovascular Diagnosis, 1992, p. 298-302, vol. 27.
Silber, "Rapid Hemostasis of Arterial Puncture Sites with Collagen in Patients Undergoing Diagnostic and Interventional Cardiac Catheterization", Clin. Cardiol., 1997, p. 981-992, vol. 20.
Smith et al., "Percutaneous Transhepatic Liver Biopsy with Tract Embolization", Radiology, 1996, p. 769-774, vol. 198.
Szikora et al., "Combined Use of Stents and Coils to Treat Experimental Wide-Necked Carotid Aneurysms: Preliminary Results", AJNR Am J Neuroradiol, Jun. 1994, p. 1091-1102, vol. 15, American Society of Neuroradiology.
Szikora et al., "Endovascular Treatment of Experimental Aneurysms with Liquid Polymers: The Protective Potential of Stents", Neurosurgery, Feb. 1996, p. 339-347, vol. 38.
Turjman et al., "Combined Stent Implantation and Endosaccular Coil Placement for Treatment of Experimental Wide-Necked Aneurysms: A Feasibility Study in Swine", AJNR Am J Neuroradiol, Jun. 1994, p. 1087-1090, vol. 15, American Society of Neuroradiology.
Yoshimoto et al., "Cerebral Aneurysms Unrelated to Arterial Bifurcations", Acta Neurochir (Wien), 1996, p. 958-964, vol. 138, Springer-Veriag, Austria.
Zins et al., "US-guided Percutaneous Liver Biopsy with Plugging of the Needle Track: A Prospective Study in 72 High-Risk Patients", Radiology, 1992, p. 841-843, vol. 184.
Ashby, Mark et al; U.S. Appl. No. 10/334,770, filed Dec. 31, 2002; entitled: "Improved System and Method for Facilitating Hemostasis with Absorbable Sponge".
Ashby, Mark et al; U.S. Appl. No. 10/421,680, filed Apr. 22, 2003; entitled: "Puncture Closure System with Pin and Pull Technique".
Ashby, "System and Method for Delivering Hemostasis Promoting Material to a Blook Vessel Puncture Site Using a Cannula,".
Berman, Howard L., et al, "Guided Direct Antegrade Puncture of the Superficial Femoral Artery," American Roentgen Ray Society, pp. 632-634 (Sep. 1986).
Berman et al, "Modification of the Cope Drainage Catheter to Facilitate Placement" AJR 146:169-170, Jan. 1986 0361-803X186/1461-0169 American Ray Society.
Correll, et al., "Certain Properties of a New Physiologically Absorbable Sponge," Proc. Soc. Exp. Biol. N.Y., 58:233 (1945).
Correll, et al., "Biologic Investigations of a New Absorbable Sponge," Surg. Gyn. and Obst., 82:585 (1945).
David, Thomas et al., "System and Method for Facilitating Hemostasis of Blood Vessel Punctures with Absorbable Sponge," United States Patent Application, p. 1-48.
Di Segni et al., "Part 1. Embolotherapy: Agents, Equipment, and Techniques" Vascular Embolotherapy, p. 29, 4, 1992.
Lim et al, "Barrier and Tensile Properties of Transglutaminase Cross-linked Gelatin Films as Affected by Relative Humidity, Temperature, and Glycerol Content," Journal of Food Science, vol. 64, NR. 4, pp. 616-622, XP009084131, (Jul. 1999).
Merriam-Webster Online Dictionary, definitions: dissolve, hydrate, p. 1-2, 2004.
Supplementary Partial European Search Report EP 02-72-0915 report date Jun. 11, 2007.
Vogelzang, Robert L., "A Modified Cope Introducing Dilator to Allow Straight Guide Wire Introduction," American Roantigen Ray Society, pp. 381-382 (Feb. 1986).

\* cited by examiner

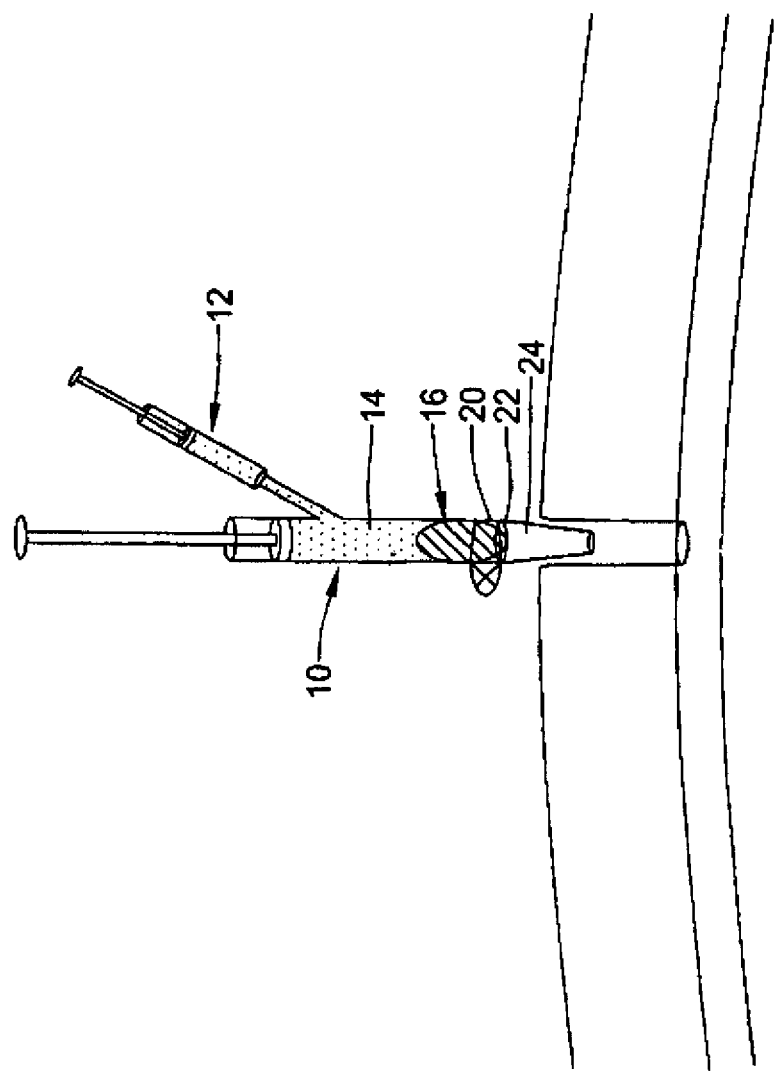

US 8,821,918 B2

CROSS-LINKED GELATIN COMPOSITION COMPRISING A WETTING AGENT

CROSS REFERENCE TO RELATED APPLICATIONS

This application is a continuation of U.S. application Ser. No. 13/477,541, filed on May 22, 2012, which is a continuation of U.S. application Ser. No. 10/068,812, filed on Feb. 4, 2002, now U.S. Pat. No. 8,187,625. This application claims priority to U.S. Provisional Patent Application Ser. No. 60/275,420, filed on Mar. 12, 2001, which application is incorporated by reference herein in its entirety.

BACKGROUND OF INVENTION

1. Field of the Invention

This invention is directed to a biocompatible, hemostatic cross-linked gelatin composition comprising cross-linked gelatin and a sufficient amount of wetting agent to permit uniform wetting of the gelatin in the presence of an aqueous solution. This invention is further directed towards methods of decreasing the hydration time of cross-linked gelatin by incorporating a biocompatible wetting agent into the gelatin. This invention further relates to a kit of parts for preparing a biocompatible, hemostatic cross-linked gelatin composition comprising a sterile syringe and non-hydrated, biocompatible, pledget comprising a cross-linked gelatin and a wetting agent.

2. References

The following patent applications and patents are cited and/or referenced in this application as superscript numbers:

[1] Correll, et al., Proc. Soc. Exp. Biol. N.Y., 58:233 (1945).
[2] Correll, et al., Surg. Gyn. and Obst., 82:585 (1945).
[3] Correll, et al., U.S. Pat. No. 2,465,357, Therapeutic Sponge and Method of Making, issued Mar. 29, 1949.
[4] Correll, et al., U.S. Pat. No. 2,507,244, Surgical Gelatin Dusting Powder and Process for Preparing Same, issued May 9, 1950.
[5] Studer, et al., U.S. Pat. No. 2,558,395, Undenatured Gelatin Hemostatic Sponge Containing Thrombin, issued Jun. 26, 1951.
[6] Sieger, et al., U.S. Pat. No. 2,899,362, Hemostatic Sponges and Method of Preparing Same, issued Aug. 11, 1959.
[7] Song, et al., U.S. Pat. No. 5,399,361, Collagen-containing Sponges as Drug Delivery Compositions for Proteins, issued Mar. 21 1995.
[8] Cragg, et al., U.S. Pat. No. 6,071,301, Device and Method for Facilitating Hemostasis of a Biopsy Tract, issued Jun. 6, 2000.
[9] Cragg, et al., U.S. Pat. No. 6,086,607, Device and Method for Facilitating Hemostasis of a Biopsy Tract, issued Jul. 11, 2000.
[10] Cragg, et al., U.S. Pat. No. 6,162,192, System and Method for Facilitating Hemostasis of Blood Vessel Punctures with Absorbable Sponge, issued Dec. 19, 2000.
[11] Pawelchak, et al., U.S. Pat. No. 4,292,972, Lyophilized Hydrocolloid Foam, issued Oct. 6, 1981.
[12] Sawyer, U.S. Pat. No. 4,238,480, Method for Preparing an Improved Hemostatic Agent and Method of Employing the Same, issued Dec. 9, 1980.
[13] Sawyer, U.S. Pat. No. 4,404,970, Hemostatic Article and Method for Preparing and Employing the Same, issued Sep. 20, 1983.

All of the above references are herein incorporated by reference in their entirety to the same extent as if each individual reference was specifically and individually indicated to be incorporated by reference in its entirety.

3. State of the Art

Cross-linked gelatin, often in the form of gelatin foam, gelatin film or gelatin sponges, has been used as a hemostatic agent since its development by Correll in 1945.[1-4] Such hemostatic sponges or foams are used routinely to pack wounds, absorb blood and stop bleeding. They are often left in place to be bioabsorbed over a period of weeks to months. In addition, medicaments, such as antibiotics, growth factors and thrombus enhancing agents, have been incorporated into the cross-linked gelatin to enhance the in vivo properties of the composition.[5-7]

To use, the hemostatic sponge is placed onto or into the wound, whereupon it absorbs blood or other fluids, expands to pack and compress the wound, and initiates a rapid clotting response. However, to achieve complete fluid absorption, rapid expansion, effective wound compression, and vigorous clotting action, the sponge must first be pre-hydrated or wetted, usually with sterile saline, before placement in the wound. This pre-hydration step, often accompanied with gentle compression and/or massaging of the sponge, can be time consuming and troublesome, often yielding non-uniform results at a critical moment in patient care. (See, for example, Directions for Use provided with Gelfoam®—available from Pharmacia Upjohn).

The hydrated sponge can then be compressed by hand and inserted or tamped into the wound. One particular wound suitable for use by hydrated sponges is a puncture site such as a puncture wound resulting from catheter insertion or a biopsy needle. When so used, the art describes ejection of a pledget of cross-linked gelatin from a syringe into the puncture site.[8-10]

Critical to the ejection process is the flowability of the pledget from the syringe assembly and retention of its structural integrity during insertion into the body. Specifically, ejection of the pledget from the syringe assembly is preferably conducted with, at most, moderate pressure to ensure accurate placement in vivo. Efficient ejection of the pledget, in turn, relates to the flowability of the cross-linked gelatin through the syringe assembly. Higher fluid content pledgets are believed to correlate with enhanced flowability and, accordingly, it is desirable to maintain as high a fluid absorbability content in the sterilized pledget as possible.

Likewise, it is critical that the structural integrity of the pledget is substantially maintained as it is ejected from the syringe assembly when placed in vivo in order to ensure that portions of the pledget are not torn or otherwise separated from the pledget. This criticality is particularly important when the pledget is placed over a blood vessel puncture in order to avoid unintended thrombosis of the vessel. Structural integrity of the gelatin composition of the pledget under pressure is believed to correlate with the tensile strength of the composition and, accordingly, it is desirable to maintain as high a tensile strength in the sterilized pledget as possible.

In addition, it is desirable to perform hydration of the pledgets in the sterile environment of an injection syringe or syringe assembly by addition of a sterile saline solution to the syringe. Such a hydration process is complicated by the potential of distortions in the pledget due to a lack of uniformity and consistency in the rate of hydration of the pledget. Such distortions could cause unanticipated difficulties in fitting the pledget into the identified wound, e.g., puncture. In addition, the length of time normally needed to hydrate the pledget would typically prohibit such a hydration process.

Accordingly, it is desired to obtain a quicker, more uniform hydration of the pledget to ensure predictability of the size and shape of the pledget and to facilitate hydration of the pledget inside the injection syringe.

SUMMARY OF THE INVENTION

This invention is directed to a biocompatible, hemostatic, cross-linked gelatin composition which has a wetting agent incorporated therein. In particular, this invention is directed to a biocompatible material comprising a cross-linked gelatin and a sufficient amount of wetting agent to permit uniform wetting of the gelatin in the presence of an aqueous solution. This invention further relates to methods of using this composition to decrease the hydration time of a hemostatic, cross-linked gelatin composition. This invention further relates to a kit of parts for preparing a biocompatible, hemostatic, cross-linked gelatin composition comprising a sterile syringe and non-hydrated, biocompatible, pledget comprising a cross-linked gelatin and a wetting agent.

Applicants have surprisingly and unexpectedly found that wetting agents can be incorporated into a cross-linked gelatin composition, improving their use as, e.g., a hemostatic sponge.

Applicants have further surprisingly found that the incorporation of wetting agents into a hemostatic, cross-linked gelatin composition decreases the hydration time needed to prepare the gelatin for use. Incorporation of the wetting agent into the cross-linked gelatin composition provides for one or more of improved fluid absorption, gelatin expansion and wound compression.

Applicants have also surprisingly found that hemostatic, cross-linked gelatin compositions with wetting agents incorporated therein are more uniformly lubricated when ejected as a pledget from a syringe assembly and less likely to suffer damage to the structural integrity of the pledget. Such pledgets are also more quickly hydrated, allowing for hydration of the pledget inside the injection syringe. Further, the pledgets made according to the invention are more uniformly hydrated, and less likely to become distorted during the hydration process.

Accordingly, in one embodiment, this invention is directed to a biocompatible, hemostatic, cross-linked gelatin composition comprising a cross-linked gelatin and a sufficient amount of wetting agent to permit uniform wetting of the gelatin in the presence of an aqueous solution.

In one embodiment, the incorporation of the wetting agent into the cross-linked gelatin can be achieved by mixing or impregnating the gelatin with wetting agent prior to foaming. In this embodiment, the wetting agent can comprise from about 0.01 to 10 weight percent of the gelatin and preferably from about 0.1 to 10 weight percent.

In another embodiment, the incorporation of the wetting agent into the cross-linked gelatin can be achieved by coating the wetting agent over the surface of a gelatin sponge. In this embodiment, a solution of wetting agent and liquid solvent carrier is prepared wherein the wetting agent comprises from about 0.01 to 20 percent of the solution and preferably from about 1 to 10 weight percent. The solution is coated over the surface of the sponge, then the liquid solvent carrier is evaporated. After evaporation, the wetting agent comprises from about 0.01 to about 5 weight percent of the gelatin sponge and preferably from about 0.1 to about 5 weight percent.

In both embodiments, the biocompatible, hemostatic sponge can be bioabsorbable. The sponge can also include one or more compositions selected from the group consisting of growth factors, thrombus enhancing agents, and antimicrobial agents.

In one of its method aspects, the invention is directed to a method for decreasing the hydration time of a cross-linked gelatin composition which method comprises, prior to hydration of said cross-linked gelatin, incorporating a biocompatible wetting agent with said cross-linked gelatin.

The biocompatible, hemostatic sponge of the present invention can be sterilized and packaged to facilitate use in surgical procedures.

Accordingly, in another of its aspects, this invention is directed to a kit of parts for preparing a biocompatible, hemostatic, cross-linked gelatin composition comprising a syringe or syringe assembly and a non-hydrated pledget, said pledget comprising a cross-linked gelatin and wetting agent.

BREIF DESCRIPTION OF THE DRAWINGS

FIG 1. is a side view of a hemostatic compound delivery system.

DETAILED DESCRIPTION OF THE INVENTION

This invention is directed to a biocompatible, hemostatic, cross-linked gelatin composition which has a wetting agent incorporated therein. In particular, this invention is directed to a biocompatible material comprising a cross-linked gelatin and a sufficient amount of wetting agent incorporated therein to permit uniform wetting of the sponge in the presence of an aqueous solution and to methods of using this composition to decrease the hydration time of the gelatin composition. Prior to describing this invention in further detail, the following terms will first be defined.

Definitions

As used herein, the following terms have the following meanings:

The term "cross-linked gelatin" refers to well known gelatin foams or sponges which are cross-linked with a conventional cross-linking agent such as formaldehyde as described in the art by Correll.sup.1-3 The term "cross-linked gelatin composition" refers to compositions comprising cross-linked gelatin. Such compositions often include other components such as a medicament.sup.8-10 or a second polymer such as collagen.sup.13 and starch.sup.6.

The term "growth factors" refers to those medicaments which are conventionally employed to facilitate tissue growth such as the endothelial wall of a punctured blood vessel or biopsy tract. Examples of suitable growth factors include PDGF, EGF, FGF, IGF's 1 and 2, TGF and the like.

The term "thrombus enhancing agents" refers to those medicaments which are conventionally employed to facilitate thrombus formation at a puncture site such as at the endothelial wall of a punctured blood vessel or a biopsy tract. Examples of suitable thrombus enhancing agents include thrombin, fibrinogen, Factor XIII and other coagulation factors.

The term "antimicrobial agent" refers to agents which destroy microbes (i.e., bacteria, fungi, viruses and microbial spores) thereby preventing their development and pathogenic action. Preferred antimicrobial agents include antibiotics and antiviral agents and, in particular, antibiotics. Other preferred antimicrobials include, for example, iodine containing materials such as PVP-I.sub.2, chlorhexidene, and the like.

The term "packaging element" refers to those packaging components used to encase the cross-linked gelatin and include, by way of example, boxes, syringes, envelopes, tubings, catheters, introducers and the like. The packaging elements may comprise glass, plastic, ceramics, cardboard, paper products and the like.

The term "wetting agent" refers to a biocompatible agent which facilitates or enhances the hydration or lubrication of a hemostatic sponge. Examples of suitable wetting agents include polyoxyalkylenes (such as BASF Pluronics, UCC Carbowaxes, PEGs), ether capped polyoxyalkylenes, e.g., polyoxyethylene lauryl ether, ester capped polyoxyalkylenes, e.g., polyoxyethylene stearate, sorbitan esters (such as certain products called Span and Tween), phosphatides (such as lecithin), alkyl amines, glycerin, water soluble polymers such as polyethylene oxides, carboxymethyl cellulose, polyvinyl alcohol, and polyvinyl pyrrolidone, surfactants such as alkyl ($C_6$-$C_{20}$) sulfate salts, e.g., sodium lauryl sulfate, aryl ($C_6$-$C_{10}$) sulfate salts, and alkaryl ($C_7$-$C_{24}$) sulfate salts, and the like.

Compositions

The compositions of this invention include biocompatible hemostatic, cross-linked gelatin compositions comprising a cross-linked gelatin composition and a sufficient amount of wetting agent to permit uniform wetting of the gelatin in the presence of an aqueous solution.

The wetting agent is utilized in an amount sufficient to enhance the hydration and/or lubrication of the composition. When the wetting agent is incorporated into the cross-linked gelatin, the wetting agent will comprise from about 0.01 to about 10 weight percent based on the total weight of the composition and preferably from about 0.1 to 10 weight percent. When the wetting agent is coated onto the surface of the cross-linked gelatin, the wetting agent will comprise from about 0.01 to about 20 weight percent, based on the total weight of the applied solution (preferably from about 1 to 20 weight percent), and 0.01 to 5 weight percent based on the total weight of the gelatin composition after evaporation of the liquid solvent of the applied solution (and preferably from about 0.1 to 5 weight percent).

In a preferred embodiment, the cross-linked gelatin composition further comprises a medicament such as an antimicrobial agent (e.g., an antibiotic), growth factors, thrombus enhancing agents, and the like or a property modifying agent such as a wetting agent. Mixtures of medicaments and property modifying agents can also be used. Suitable medicaments can be mixed with or impregnated into the cross-linked gelatin composition prior to sterilization procedures.

When employed, the medicament is utilized in an amount sufficient for its intended purpose, e.g., an antimicrobially effective amount, an amount sufficient to induce thrombus formation, and an amount sufficient to promote growth. The specific amount employed relates to the effectiveness of the medicament, the disease condition of the patient being treated, the age and weight of the patient, the location of the disease and other factors well within the purview of the attending clinician.

Prior to administration of the biocompatible, hemostatic, cross-linked gelatin to the patient, the gelatin will be sterilized. Sterilization can be achieved by, for example, heat or E-beam sterilization. Biocompatible wetting agents will typically be incorporated into or coated onto the cross-linked gelatin composition prior to the sterilization procedure. E-beam sterilization of a cross-linked gelatin composition is described in U.S. Provisional Patent Application Ser. No. 60/275,391, filed Mar. 12, 2001, entitled "Methods for Sterilizing Cross-Linked Gelatin Compositions" (Attorney Docket No. 032005-093), which application is incorporated herein by reference in its entirety. Heat sterilization of a cross-linked gelatin composition is described in U.S. Pat. No. 2,465,357.sup.3

In the embodiment, described in FIG. 1, a pledget of the cross-linked gelatin composition of the present invention can be inserted into a syringe assembly 10 comprising a holding chamber 14, an injection port which comprises a luer hub 20, and an ejection port 22 which is attached to a cannula 24. The syringe assembly containing the pledget 16 can be packaged and sterilized. Then, sterile saline 12 can be added to the holding chamber 14 in a sufficient amount to hydrate the pledget 16. Once the pledget is hydrated, the pledget 16 can be transferred into the cannula 24 attached to the ejection port 22.

The incorporation of wetting agents into the cross-linked gelatin composition can allow for rapid, uniform wetting of the gelatin and elimination of the pre-hydration process. The wetting agent can be added and dissolved (or dispersed) directly into the hemostat chemical formulation, preferably just before the foaming process. An amount of wetting agent ranging from about 0.01 to 10 percent based on the weight of the gelatin material, and preferably from 0.1 to 10 percent, can be used. Processes for manufacturing a hemostatic sponge are disclosed in U.S. Pat. No. 2,465,357.sup.3 and U.S. Pat. No. 2,507,244.sup.4.

Alternatively, the wetting agent could be dissolved (or dispersed) in a non-aqueous liquid solvent (e.g., ethanol, isopropanol, acetone and the like) coated onto the cross-linked gelatin composition and the liquid solvent removed by evaporation. In another embodiment, the wetting agent and liquid solvent mixture could be applied onto the gelatin composition and the foam compressed. The liquid solvent would then be removed by evaporation. When the wetting agent is coated over the gelatin composition, the concentration of the wetting agent in the liquid solvent is preferably from about 0.01 to 20 percent and preferably from 1 to 20 weight percent and more preferably 1 to 10 weight percent.

Suitable biocompatible wetting agents are commercially available and include, for example, sodium lauryl sulfate, Pluronic F-68, Pluronic F-38, Pluronic P-105, Pluronic-10R5, Tween 20, Tween 60, Tween 85, Brij 35, Brij 78, Myrj 52, PEG 600, glycerin and the like.

In addition, biocompatible wetting agents can be incorporated into biocompatible collagen hemostatic sponges (e.g., Actifoam™) to improve their wetting times in the manner and concentrations set forth above. Suitable wetting agents include Tween 20 (1% in isopropanol) and Pluronic P-105 (1% in isopropanol).

EXAMPLES

The following examples are set forth to illustrate the claimed invention and are not to be construed as a limitation thereof.

In these examples, unless otherwise indicated, all temperatures are in degrees Centigrade and all percents are weight percents based on the total weight of the composition. Similarly, the following abbreviations are employed herein and are as defined below. Unless defined, the abbreviations employed have their generally accepted meaning:

cc=cubic centimeter
cm=centimeter
EtOH=ethanol
g=gram
IPA=isopropyl alcohol
min.=minute
mm=millimeter mL=milliliters
pcs=pieces
RH=relative humidity
RO water=reversed osmosis water
RPM=rotations per minute
sec=seconds
wt=weight

Example 1

Comparison of Hydration Time of Cross-Linked Gelatin with Wetting Agent Incorporated Therein Vs. Cross-Linked Gelatin without Wetting Agent The purpose of this example is to demonstrate the feasibility of different agents in reducing the hydration time of a cross-linked gelatin having a variety of candidate wetting agents incorporated into the gelatin prior to foaming (Gelatin Composition 1A). In this example, the surfactant was added to the solution used to prepare the cross-linked gelatin foam.

The results of the amount of time required to wet the gelatin was compared to the hydration time of a cross-linked gelatin which does not have any candidate wetting agents incorporated therein (Comparative Gelatin Composition 1B).

A. Preparation of Gelatin Composition 1A

Gelatin Composition 1A was prepared as follows. A stock solution of 5% pigskin gelatin in purified bottled water was prepared by heating to 60.degree. C. with constant stirring. The solution was cooled to 37.degree. C. and 0.01% formalin added. This was incubated for two hours. To produce a 10% surfactant to gelatin ratio (i.e., 10% loading), 1.5 grams of surfactant was dissolved in 20 grams of water, and this solution added to 280 gram aliquots of the stock gelatin solution.

Foam was produced by whipping air into the warm mixture for about 2 minutes using a kitchen blender. The whipping ceased when the foam peaked. The gelatin foam was then transferred to screens and contained within metal shells until firm, about 10-15 minutes. The foam was dried at 32.2.degree. C. (90.degree. F.) and 18% RH, which took about 24-36 hours. Test samples were prepared by cutting the skin from the dried foam buns and cutting cubes of about 1.5-2.0 cm from central locations in the bun. For additional information regarding the preparation of such gelatin compositions, see U.S. Pat. Nos. 2,465,357 and 2,507,244.

The following candidate wetting agents were each incorporated into the gelatin prior to foaming:
1. Polyacrylamide (weight average molecular weight of about 1500) (as a sample of an cationic wetting agent)
2. Sodium lauryl sulfate (as a sample of a anionic wetting agent)
3. Pluronic F-68 (poly(ethylene oxide)-co-(propylene oxide) block), (as a sample of a non-ionic wetting agent—number average molecular weight of about 8400) (commercially available from BASF Corp.)
4. Tween 20 (polyoxyethylene sorbitan monolaurate), (as a sample of a non-ionic wetting agent—molecular weight of approximately 1227)
5. PEG (600) (poly(ethylene glycol), (as a sample of a non-ionic wetting agent—molecular weight of about 600)
6. Glycerin (as a sample of a non-ionic wetting agent)

B. Preparation of Comparative Gelatin Composition 1B

Comparative Gelatin Composition 1B was prepared as above except for omission of the wetting agent.

C. Comparison of the Foam Properties and Hydration Time of Cross-Linked Gelatin with Wetting Agent Incorporated Therein Vs. Gelatin Without Wetting Agent (1) Foam Properties Most of the gelatin compositions produced a smooth, white, meringue-like foam, which dried into a high, rigid, compressible bun.

Gelatin Compositions 1A produced with lauryl sulfate, Pluronic F-68, Tween 20 and 30% lauryl sulfate candidate wetting agents were softer and less compressible. These compositions also displayed some loss of foam height and an increase in cell size and voids. The Tween 20 and 30% lauryl sulfate formulations demonstrated the most collapse and increase in cell size and voids.

(2) Hydration

Table 1 sets forth the hydration times for the Gelatin Compositions 1A and the Comparative Gelatin Compositions. Hydration was tested in both uncompressed and compressed (comp.) foams. The concentration of candidate wetting agent in each composition is indicated as a percent loading. Specifically, the percent loading refers to the weight percent of the wetting agent based on gelatin in the composition before foaming based on a 300 mL solution containing 5% gelatin.

The Gelatin Compositions 1A with the lauryl sulfate (30% loading), Tween 20 and Pluronic F-68 wetting agents yielded a startling reduction in hydration time of about 3 to 10 seconds (versus 6 minutes for the Comparative Gelatin Composition 1B (control)). The amount of water absorbed was somewhat reduced for the 30% lauryl sulfate containing sample. It was basically unchanged for the other two compositions.

Unless otherwise noted, all samples were the aggregate of 3 pieces.

TABLE 1

Hydration Times for Gelatin Compositions 1A and Comparative Gelatin Compositions

| Wetting Agent | Hydration Time (min) | Dry Weight (g) | Wet Weight (g) | Wet/Dry (3 pcs) |
|---|---|---|---|---|
| Comparative Gelatin Composition 1B (0% loading) | 6.5-7.0 | 0.13 | 3.74 | 29 |
| Comparative Gelatin Composition 1B (0% loading) (Comp 15 - 2 mm) | 6.0-6.5 | 0.12 | 4.23 | 35 |
| Gelatin Composition 1A Polyacrylamide Wetting Agent (10% loading) | >20 | 0.14 | ND | ND |
| Gelatin Composition 1A Polyacrylamide Wetting Agent (10% loading) (Comp 15 - 2 mm) | >20 | 0.16 | ND | ND |
| Gelatin Composition 1A Lauryl sulfate Wetting Agent (10% loading) | 45 sec | 0.24 | 4.30 | 18 |
| Gelatin Composition 1A Lauryl sulfate Wetting Agent (10% loading) (Comp 20 - 2 mm) | 45 sec | 0.44 | 7.55 | 17 |
| Gelatin Composition 1A Lauryl sulfate Wetting Agent (30% loading) | 10-15 sec | 0.18 | 3.01 | 17 (1 pc) |
| Gelatin Composition 1A Lauryl sulfate Wetting Agent (30% loading) (Comp 15 - 1 mm) | 10 sec | 0.17 | 3.04 | 18 (1 pc) |
| Gelatin Composition 1A Pluronic F-68 Wetting Agent (10% loading) | 3-5 sec | 0.17 | 4.13 | 24 |
| Gelatin Composition 1A Pluronic F-68 Wetting Agent (10% loading) (Comp 15 - 3 mm) | 3.5 sec | 0.15 | 3.73 | 25 |

TABLE 1-continued

Hydration Times for Gelatin Compositions 1A and Comparative Gelatin Compositions

| Wetting Agent | Hydration Time (min) | Dry Weight (g) | Wet Weight (g) | Wet/Dry (3 pcs) |
|---|---|---|---|---|
| Gelatin Composition 1A Tween 20 Wetting Agent (10% loading) | 5 sec | 0.37 | 10.90 | 29 |
| Gelatin Composition 1A Tween 20 Wetting Agent (10% loading) (Comp 10 - 2 mm) | 5 sec | 0.28 | 8.08 | 29 |
| Gelatin Composition 1A PEG 600 Wetting Agent (10% loading) | 4.5 | 0.18 | 5.15 | 29 |
| Gelatin Composition 1A PEG 600 Wetting Agent (10% loading) (Comp 20 - 2 mm) | 3.5 | 0.22 | 6.01 | 27 |
| Gelatin Composition 1A Glycerin Wetting Agent (10% loading) | 4.5 | 0.25 | 5.13 | 21 |
| Gelatin Composition 1A Glycerin Wetting Agent (10% loading) (Comp 20 - 2 mm) | 3.5 | 0.25 | 6.71 | 27 |
| Comparative Gelatin Composition 1B (0% loading) | 5.5 | 0.16 | 4.72 | 30 |

The wet/dry ratio reported is the wet weight over the dry weight which provides a ratio of the amount of water absorbed per unit weight of dry material.

The above data indicates that all of the candidates used, with the exception of polyacrylamide, act as wetting agents per this invention. On the other hand, the increase in wetting time provided by using polyacrylamide indicates that this material is not a suitable wetting agent.

The above data of the different agents used, little or no change in the wet/dry ratio occurred with the use of either Tween 20 or PEG 600; modest lowering of the wet/dry ratio occurred with the use of Pluronic F-68 and Glycerin; and somewhat greater lowering of the wet/dry ratio occurred with the use of lauryl sulfate.

Example 2

Comparison of Hydration Times Cross-Linked Gelatin Compositions with Wetting Agent Coating Vs. Cross-Linked Gelatin Compositions without a Wetting Agent Coating The purpose of this example is to demonstrate the reduction in hydration time of a cross-linked gelatin composition containing different non-ionic wetting agents (Gelatin Composition 2A) and forming a surfactant coating on the pre-formed cross-linked gelatin foam composition. Specifically, in this example, the wetting agents were coated onto the cross-linked gelatin composition in the following manner: the wetting agent was added to a solvent, the cross-linked gelatin composition was added to the resulting solution, the soak time used was 10 seconds or 1 minute, as indicated below, the cross-linked gelatin composition was removed, excess liquid drained, and then the solvent was allowed to evaporate.

The hydration time required to wet these compositions was compared to the hydration time of a cross-linked gelatin composition without such a wetting agent coating (Comparative Gelatin Composition 2B (no coating) and Comparative Gelatin Composition 2C (carrier solvent coating)).

A. Preparation of Gelatin Composition 2A

Gelatin Composition 2A was prepared as follows. First, Comparative Gelatin Composition 1B, as set forth in Example 1, was prepared.

Second, ten percent solutions of each of the following wetting agents were prepared in isopropanol (2-Propanol, ACS reagent (Aldrich Cat. #19076-4)) in 30 cc screw cap vials.

1. Tween 20 (polyoxyethylene (20) sorbitan monolaurate) (Aldrich Cat. #27434-8)
2. Tween 60 (polyoxyethylene (20) sorbitan monostearate) (Aldrich Cat. #37425-3)
3. Tween 85 (polyoxyethylene (20) sorbitan trioleate) (Aldrich Cat. #38890-4)
4. Brij 35 (polyoxyethylene (23) lauryl ether) (Aldrich Cat. #85836-6) (Sigma)
5. Myrj 52 (polyoxyethylene (40) stearate) (Aldrich Cat. #P3440) (BASE)
6. Brij 78 (polyoxyethylene (23) steryl ether) (Sigma #23600-4)

A 2×0.2×0.0.6 cm piece of Gelatin Composition 2A was placed into each vial and the vial inverted to soak the composition with the solution. This was repeated for each solution. Two contact/soak times were employed, 10 seconds and one minute.

The coated Gelatin Compositions 2A were then removed, drained of excess liquid and air dried overnight.

B. Preparation of Comparative Gelatin Composition 2B and 2C

Comparative Gelatin Composition 2B (untreated) was prepared as set forth for Comparative Gelatin Composition 1B in Example 1.

Comparative Gelatin Composition 2C (carrier solvent coating) was prepared as follows. A 2.times.2.times.0.6 cm piece of Comparative Gelatin Composition 1B (as set forth in Example 1) was placed into a 30 cc screw cap vial of isopropanol and the vial inverted to soak the composition with the solution. Two contact/soak times were employed, 10 seconds and one minute. After soaking, the gelatin compositions were then air dried overnight.

C. Comparison of Hydration Times

Dry samples of each of the Gelatin Compositions 2A and the Comparative Gelatin Compositions 2B and 2C were compressed to about 0.1 cm and dropped into a 250 mL beaker containing 100 mL of RO water.

The time for each gelatin composition to reach full hydration was measured with a digital stopwatch. Hydrated samples were weighed and reweighed to assure full hydration. Hydration was also determined by monitoring when the composition turned from opaque to translucent.

The results of this evaluation are shown in Table 2. Where two values are given, duplicate runs were made.

TABLE 2

Hydration Times for Gelatin Composition 2A and Comparative Gelatin Compositions 2B and 2C

| Gelatin Composition | Soak Time in Wetting Agent Solution | Hydration Time | Wet/Dry Wt. |
|---|---|---|---|
| Comparative Gelatin Composition 2B | 0 | 6, 6 min | 28, 33 |
| Gelatin Composition 2A Tween 20 Wetting Agent | 10 sec | 20, 25 sec | 49, 35 |
| Gelatin Composition 2A Tween 20 Wetting Agent | 1.0 min | 15, 20 sec | 49, 58 |

TABLE 2-continued

Hydration Times for Gelatin Composition 2A and
Comparative Gelatin Compositions 2B and 2C

| Gelatin Composition | Soak Time in Wetting Agent Solution | Hydration Time | Wet/Dry Wt. |
|---|---|---|---|
| Gelatin Composition 2A Tween 60 Wetting Agent | 10 sec | 3, 1.5 min | 41, 44 |
| Gelatin Composition 2A Tween 60 Wetting Agent | 1.0 min | 24, 35 sec | 38, 31 |
| Gelatin Composition 2A Tween 85 Wetting Agent | 10 sec | 30, 30 sec | 41, 45 |
| Gelatin Composition 2A Tween 85 Wetting Agent | 1.0 min | 35, 35 sec | 46, 34 |
| Gelatin Composition 2A Myrj 52 Wetting Agent | 10 sec | 15, 20 sec | 38, 26 |
| Gelatin Composition 2A Myrj 52 Wetting Agent | 1.0 min | 40, 40 sec | 37, 29 |
| Gelatin Composition 2A Brij 35 Wetting Agent | 10 sec | 15, 15 sec | 55, 42 |
| Gelatin Composition 2A Brij 35 Wetting Agent | 1.0 min | 40, 40 sec | 52, 33 |
| Gelatin Composition 2A Brij 78 Wetting Agent | 10 sec | 15, 15 sec | 38, 39 |
| Gelatin Composition 2A Brij 78 Wetting Agent | 1.0 min | 20, 20 sec | 43, 42 |
| Comparative Gelatin Composition 2C | 10 sec | 3 min | 40 |
| Comparative Gelatin Composition 2C | 1.0 min | 3 min | 40 |

The wet/dry ratio reported is the wet weight over the dry weight which provides a ratio of the amount of water absorbed per unit weight of dry material.

All samples of cross-linked gelatin, treated or not, yielded very large and similar uptakes for water (wet/dry weight). Also, as evident above, the best wetting agents were deemed those that produced the most rapid hydration, e.g., Tween 20, Brij 35 and Brij 78.

Example 3

Demonstration of Improved Hydration Time for Cross-Linked Gelatins with Wetting Agent Coatings Containing Ethanol and Isopropanol Carrier Solvents The purpose of this example is to demonstrate that the improved hydration time achieved for cross-linked gelatins coated with non-aqueous wetting agents as per Example 2 above were independent of the solvent used to coat the gelatin.

Specifically, gelatin composition 3A was prepared in the same manner as gelatin composition 2A. The wetting agent coating solution comprises a selected wetting agent and a carrier solvent of either ethanol or isopropanol. Soak contact time of the foam in the wetting solution was about 10 seconds each.

After the coating layer has dried, the gelatin compositions were compressed and soaked in a 250 mL beaker containing 100 mL of RO water. The hydration times were measured as in Example 2.

The specific wetting agents employed were as follows:
1. Tween 20 (polyoxyethylene (20) sorbitan monolaurate) (Aldrich Cat. #27434-8)
2. Pluronic F-68 (poly(ethylene oxide)-co-(propylene oxide) block), (as a sample of a non-ionic wetting agent—average molecular weight of about 8400) (commercially available from BASF Corp.)
3. Pluronic P-105 (poly(ethylene oxide)-co-(propylene oxide) polymer), (as a sample of a non-ionic wetting agent—average molecular weight of about 6500) (commercially available from BASF Corp.)
4. Pluronic-10R5 (poly(ethylene oxide)-co-(propylene oxide) polymer), (as a sample of a non-ionic wetting agent—average molecular weight of about 4550) (commercially available from BASE Corp.).
5. Pluronic-F38 (poly(ethylene oxide)-co-(propylene oxide) block), (as a sample of a non-ionic wetting agent—average molecular weight of about 5000) (commercially available from BASE Corp.).

Hydration times for the compositions are set forth in Table 3 below. Where multiple values are given, multiple runs were made.

TABLE 3

Hydration Times for Gelatin Compositions 3A

| Wetting Agent Used in Gelatin Composition 3A | Carrier Solvent | Hydration Times |
|---|---|---|
| Tween 20 | 3% ETOH | 10, 15; 10, 15, 15 sec |
| Tween 20 | 3% IPA | 20, 20; 10, 10, 15 sec |
| Tween 20 | 10% ETOH | 10, 10 sec |
| Tween 20 | 10% IPA | 10, 10 sec |
| F-38 | 3% ETOH | 40, 40, 40 sec |
| F-38 | 3% IPA | 30, 45, 45 sec |
| F-68 | 3% ETOH | 30, 45, 45 sec |
| F-68 | 3% IPA | 20, 25, 20 sec |
| P-105 | 3% ETOH | 10, 15, 10 sec |
| P-105 | 3% IPA | 10, 10, 10 sec |
| 10R5 | 3% ETOH | 10, 20, 20 sec |
| 10R5 | 3% IPA | 10, 10, 10 sec |

The average wet/dry ratio for the above samples was approximately 44 with a range of from 39-56 wherein this ratio is calculated by the wet weight over the dry weight which provides a ratio of the amount of water absorbed per unit weight of dry material.

The above data demonstrates that there is no appreciable difference in the hydration time of the coated cross-linked gelatin using different solvents to coat the gelatin.

However, the solvent employed should be non-aqueous to the extent that water irreversibly damages the foam. Preferably, the non-aqueous solvent is ethanol and/or isopropanol since methanol causes some degradation of the foam properties and acetone exhibits a disagreeable odor.

Example 4

Hydration Times for Cross-Linked Gelatin Compositions with Wetting Agent Coating of Varying Concentrations This example examines the effect of wetting agent concentration on hydration time used to coat the cross-linked gelatin composition.

Specifically, cross-linked gelatin compositions with wetting agent coatings were prepared as in Example 2. The wetting agent coating solutions were prepared with concentrations of the selected wetting agents of 0.1, 1.0, 3.0 and 10.0%. The hydration times were measured on compressed samples, in the manner set forth in Example 2.

All of the wetting agents and concentrations demonstrated rapid hydration times, although at the highest concentration of 10%, the hydration time was somewhat reduced. The results are set forth in Table 4 below. Where multiple values are given, multiple runs were made.

TABLE 4

Hydration Times for Cross-Linked Gelatin Compositions with Wetting Agent Coatings of Varying Concentrations

| Wetting Agent Used in Coating | Hydration Times at Wetting Agent Concentration | | | |
|---|---|---|---|---|
| | 0.10% | 1.00% | 3.00% | 10.00% |
| Tween 20 | 15, 10; 60, 25, 15 sec | 15, 10; 15, 10; 10 sec | 20, 10 sec | 20, 10 sec |
| Brij 35 | 10, 10, 10; 35, 20, 20 sec | 15, 10, 10; 30, 20 sec | 10, 20, 15 sec | 20, 30, 30 sec |
| Brij 78 | 10, 15, 10 sec | 10, 10; 25 sec | 10, 10 sec | |
| P-105 | 15, 15 sec | 10, 10; 10 sec | 10, 10 sec | |
| 10R5 | 15, 15 sec | 10, 10 sec | 10, 10 sec | |

The wet/dry ratio reported is the wet weight over the dry weight which provides a ratio of the amount of water absorbed per unit weight of dry material.

The above data demonstrates that the concentration of wetting agent employed in the coating solution does not materially affect the hydration time of the coated cross-linked gelatin.

Example 5

Hydration Times for Cross-Linked Gelatin Compositions with Wetting Agent of Varying Concentrations Incorporated Therein This example evaluates the effect of wetting agent concentration used during the formation of a gelatin foam composition on both the hydration time and the wet/dry ratio. This example differs from the previous example in that the wetting agent is added to the composition prior to foam formation as per Example 1 rather than coating a prior formed cross-linked gelatin foam with the wetting agent as per Examples 2-4.

Specifically, cross-linked gelatin compositions with wetting agents incorporated therein were prepared as in Example 1 except that 0.02 weight percent of formalin was used and wherein the wetting agent was added to the gelatin composition prior to foam formation. The wetting agent coating solutions were prepared with concentrations set forth in Table 5.

The hydration times for these gelatin compositions were measured by manually compressing each cut sample and dropping it into a beaker containing 150 mL of tap water. Hydration was complete when the foam turned translucent and were measured on compressed samples, in the manner set forth in Example 2. Hydration time of a control, similar to Comparative Gelatin Example 2B, was also measured.

The hydration times are set forth in the Table 5 below.

TABLE 5

| Wetting Agent | Concentration | Foam Wet | Foam Dry | Hydration Time | Wt. Wet/Dry |
|---|---|---|---|---|---|
| Tween 20 | 5% | ¾ in. | ⅜ in. | 2-3 sec | NA |
| Tween 20 | 3% | ½ in. | ⅜ inc. | 2-3 sec | 23.4 |
| Tween 20 | 1% | ¾ in. | ¼ in. | 2-3 sec | 24.0 |
| Tween 20 | 0.10% | ¾ in. | ⅝ in. | 5 sec | 41.5 |
| Tween 60 | 3% | no foam | | NA | NA |
| Tween 85 | 3% | no foam | | NA | NA |
| Myrj 52 | 3% | no foam | | NA | NA |
| Brij 35 | 3% | 1¼ in. | ¼ in. | 2-3 sec | 16.5 |
| Brij 78 | 3% | ½ in. | ⅜ in. | 2-3 sec | 12.0 |
| F-68 | 3% | 1 in. | ¼ in. | 2-3 sec | 19.7 |
| Control | 0% | 1¾ in. | 1¼ in. | 8 min | 45.8 |

These results indicate that gelatin foam compositions with wetting agents did not achieve the same level of foam formation as compared to the control. Upon drying, foam heights for these compositions were further reduced, with the lowest concentration of surfactant causing less height reduction.

The compositions with the wetting agents incorporated therein also tended to be softer and more resilient, more fibrous and with larger irregular cells than the control compositions. Again, the lowest concentration of surfactant (0.1%) gave foams closer to the control.

All gelatin foams with wetting agent incorporated therein demonstrated very rapid and complete hydration. Hydration was complete within 2-3 seconds for the surfactant gelatin samples compared to about 8 minutes for the control. At the 0.1% level, the presence of the surfactant was sufficient to dramatically improve hydration times.

Unfortunately, water uptake was significantly diminished for all surfactant samples, except those with the lowest concentration of surfactant. Mechanical strength of all the samples (wet or dry) was excellent, and equal to that of the control.

Based on the above data, when the wetting agent is incorporated prior to cross-linked gelatin foam formation, very low concentrations of wetting agent are preferred. Moreover, the data indicates minimal impact of low concentrations of wetting agent on reduced hydration time indicating that such low concentrations advantageously provide for a composition closer to control in many properties but surprisingly have excellent hydration times as compared to control.

Preferred wetting agents as demonstrated in this example utilizing the addition of wetting agent prior to foam formation should not prevent foam sponge formation of the cross-linked gelatin.

Example 6

This example demonstrates that the incorporation of a wetting agent into a gelatin composition does not deleteriously effect the clotting ability of the gelatin composition as compared to control. A partial thromboplastin test (PTT) was employed. The PTT assay is a general screening assay for the detection of coagulation abnormalities in the intrinsic coagulation pathway. This is particularly important because, notwithstanding improved hydration time, a cross-linked gelatin composition having an adverse effect on blood clotting would be contra-indicated for use, e.g., as a hemostatic sponge.

Specifically, in this example, fresh whole human blood was drawn at AppTec Laboratory Services using vacutainer tubes containing sodium citrate. The citrated whole blood was spun down. The plasma was separated from the red blood cells, pooled into a polypropylene test tube, and stored on ice. This plasma was used as the exposure medium for testing.

The comparison sample, test tube, reference material and controls were placed in polypropylene tubes and exposed to plasma (determined by the 1 mL/4 cm.sup.2 exposure ratio) for 15 minutes at 37.+-0.1.degree. C. in an agitating water bath at 60 RPM. The volume of 0.3 mL of plasma was used to saturate the test and comparison articles prior to exposure. At the end of the incubation period, the plasma was removed from the materials. The plasma samples were placed on ice and tested on the Cascade M4.

The results are set forth in Tables 6 and 7 below.

TABLE 6

| Article | Exposure Ratios | | Coagulation Time (seconds) | | |
| --- | --- | --- | --- | --- | --- |
| | Surface Area (cm²) | (mL) | Assay Values | Ave. | % of Neg Control |
| Cross-linked Gelatin - Ex. 2B | 4.0 | 1.0 | 300/226.7/300 | 275.6 | 92 |
| Gelfoam (Pharmacia-Upjohn) | 4.0 | 1.0 | 300/300/300 | 300 | 100 |
| Positive Control, Black Rubber | 4.0 | 1.0 | NA | 39.9 | 13 |
| Reference Material, Latex Tubing | 4.0 | 1.0 | NA | 174.3 | 58 |
| Negative Control, Human Plasma | NA | 1.0 | NA | 300 | NA |

TABLE 7

| Article | Exposure Ratios | | Coagulation Time (seconds) | | |
| --- | --- | --- | --- | --- | --- |
| | Surface Area (cm²) | (mL) | Assay Values | Ave. | % of Neg Control |
| Cross-linked Gelatin - Ex. 2A (0.3% Tween 20) | 4.0 | 1.0 | 300/208.2/300 | 269.4 | 90 |
| Gelfoam (Pharmacia-Upjohn) | 4.0 | 1.0 | 300/300/300 | 300 | 100 |
| Positive Control, Black Rubber | 4.0 | 1.0 | NA | 39.9 | 13 |
| Reference Material, Latex Tubing | 4.0 | 1.0 | NA | 174.3 | 58 |
| Negative Control, Human Plasma | NA | 1.0 | NA | 300 | NA |

If coagulation does not occur within 300 seconds, the result is reported as "300 sec.").

The above data demonstrates that the compositions of this invention exhibit substantially equivalent effects on clotting time as compared to control and, accordingly, it was concluded that these compositions are compatible for use as, e.g., hemostatic sponges.

Example 7

This example evaluates the histopathologic results of a total of 2 arterial femoral puncture sites from one pig, using the compositions of this invention. The objective of this evaluation was to assess the acute and chronic outcome of femoral puncture sites following closure with the compositions of this invention delivered into the tissue tract adjacent to the vessel puncture using a cannula delivery tube. The puncture wound in the right femoral artery was sealed with cross-linked gelatin composition comprising 0.1% Tween 20 obtained from solvent coating of the composition per Example 2 above. The puncture wound in the left femoral artery was sealed with cross-linked gelatin composition comprising 0.3% Tween 20 obtained from solvent coating of the composition per Example 2 above. Subsequently, approximately 2-4 weeks later, the animal was sacrificed, the arteries adjacent the femoral puncture site were excised and fixed in formalin.

Specifically, the formalin-fixed arterial explants were trimmed in the area of interest every 3 mm into 11 to 14 segments (sections 1 to 14). The sections' sequence was started at the proximal end of each explant. The sections were embedded in paraffin, sectioned at approximately 5 microns three times serially, and stained with Hematoxylin and Eosin (HE), Masson's Trichrome (MT), and Verhoeffs Van Gieson (VVG) stain, respectively. Histologic evaluation was performed and data were recorded.

A 1 to 5 grading scale was utilized, where 1 is minimal, 2 is mild, 3 is moderate, 4 is marked, and 5 is severe. Loss of endothelium was graded according to circumferential spread of the change. The change of endothelium loss spanned approximately up to 20% of the circumference in grade 1, 20-40% in grade 2, 40-60% in grade 3, 60-80% in grade 4 and more than 80% in grade 5. Necrosis of the media was graded according to depth extension. The change of media necrosis extended into approximately up to 20% of the media thickness in grade 1, 20-40% in grade 2, 40-60% in grade 3, 60-80% in grade 4 and more than 80% in grade 5.

1-Animal 3094G—Right Femoral Artery

Gross Observations: The segment of artery was 52 mm long. There were no significant gross changes in the intact explant. Trimming revealed sub-occlusive thrombosis in most sections (1 through 8) and partial thrombosis in sections 9 and 10. The delivery tract could not be seen grossly.

Microscopic Observations: The puncture site was observed in sections 9 and 10 (24 and 27 mm from origin). There was transmural laceration with regeneration and fibrosis of the edges. From these lacerated sites and the corresponding intimal areas of more proximal sections a partially organized thrombus projected into the lumen and was nearly occluding the lumen. There was mineralization of the media in a sub-intimal position (sections 1, 2, 7, 8, 9), due to localized media pressure necrosis (dystrophic mineralization). Mineralization was also observed in the organizing thrombus. There was slight to mild partial loss of endothelium in the proximal sections (sections 1-7) that was considered to be the result of erosion associated with termination catheterization. In approximately the proximal ⅔ of the explant (sections 1-10) there was fibrosis of the media, most likely due to pressure necrosis at the time of treatment. The implant was not observed. There was mature connective tissue in the adventitia possibly corresponding to the treatment tract. These microscopic observations are consistent with arterial needle puncture and healing.

2-Animal 3094G-Left Femoral Artery

Gross Observations: The segment of artery was 50 mm long. There were no significant gross changes in the intact explant.

Microscopic Observations: Transmural laceration (puncture site) was observed in section 8 (18-21 mm, recut 3) and was characterized by bifocal laceration across the vessel with proliferation of fibrous granulation tissue across the lumen dividing the pre-existing arterial wall into two symmetrically placed remnants. The residual lumen was confined to one of the arterial remnants. The lumen was constructed (moderate stenosis) by intimal fibrous proliferation at the puncture site. There was mineralization of the external elastic lamina adjacent to the laceration site. There was moderate fibrosis in the adventitia at the laceration site and in a separate area in the more distant adventitial tissue that most likely corresponds to the puncture tract. There was no residual implant material and there was no significant inflammatory response in the tract. There was minimal to mild loss of endothelium that was considered to be the result of erosion associated with termination catheterization.

The access tract produced by the catheter was found in the vascular wall in both samples as a localized fibrosis in the adventitia and focal transmural fibrosis. The left artery displayed bifocal transmural laceration and healing by fibrous connective tissue and media regeneration bridging across the lumen, indicating focal puncture through opposite sides of the vessel. There was no significant occlusive thrombosis in the left artery but focal moderate stenosis associated with intimal hyperplasia at the puncture site was present. The right artery there was sub-occlusive thrombosis that proceeded from the puncture site and extended proximally. There was evidence of pronounced architectural disruption and media necrosis due to mechanical trauma to the vessel wall at the puncture site, believed to be responsible for thrombosis. No residual foam test material was observed. These microscopic observations are consistent with arterial needle puncture and healing.

The above data demonstrates that the compositions of this invention are well tolerated in vivo.

Example 8

This example evaluates the cytotoxicity of the compositions of this invention as compared to prior art compositions, i.e., in the absence of a wetting agent. In this example, samples were tested in the ISO agarose overlay cytotoxicity test—a test well known in the art for determining cytotoxicity potential. Specifically, samples were placed onto petri dishes, in triplicate, containing agarose the surface of which contains a monolayer of L-929 mouse fibroblast cells which are sensitive to cytotoxic agents. Subsequently, the samples were evaluated for reactivity and grade depending upon the amount of cellular damage or death directly beneath and/or surrounding the material. The scoring is based on the following:

0=no zone under or around sample
1=some malformed or degenerated cells under sample
2=zone limited to area under sample
3=zone extends 0.5 to 1.0 cm beyond sample
4=zone extends greater than 1.0 cm In this example, a score of 0-2 is deemed to be non-toxic; a score of 3 is deemed to be weakly or moderately toxic; and a score of 4 is strongly toxic.

The results of this evaluation are summarized below in Table 8:

TABLE 8

| Sample | Score |
|---|---|
| Cross-linked gelatin w/o surfactant | 0 |
| Cross-linked gelatin with Tween 20 (prepared by Example 2 - isopropanol) | |
| 0.3% Tween 20 | 0 |
| 1.0% Tween 20 | 1, 1 (two triplicate runs) |
| Cross-linked gelatin with Pluronic P-105 (prepared by Example 2 - isopropanol) | |
| 0.3% Pluronic P-105 | 0, 0 (two triplicate runs) |
| 1.0% Pluronic P-105 | 0, 0 (two triplicate runs) |

The above results demonstrate that the compositions of this invention, as tested in this example, are non-cytotoxic.

From the foregoing description, various modifications and changes in the above described methods will occur to those skilled in the art. All such modifications coming within the scope of the appended claims are intended to be included therein.

The invention claimed is:

1. A kit of parts for preparing a biocompatible, hemostatic, cross-linked gelatin composition comprising:
   a sterile syringe assembly;
   a saline solution;
   a non-hydrated pledget, said pledget comprising a preformed cross-linked gelatin sponge coated by soaking the non-hydrated pledget
   in a non-aqueous solvent having a wetting agent dissolved therein;
   wherein evaporation of the non-aqueous solvent coats at least a substantial portion of the surface of the non-hydrated pledget with the wetting agent;
   wherein the wetting agent decreases hydration time of the non-hydrated cross-linked gelatin pledget.

2. The kit of claim 1, wherein the syringe assembly comprises a holding chamber, an ejection port, and a cannula.

3. The kit of claim 2, wherein the syringe assembly is adapted to combine the saline solution and the non-hydrated pre-formed cross-linked gelatin pledget including the wetting agent coated on at least a substantial portion of the surface thereof in the holding chamber and subsequently eject the cross-linked gelatin pledget.

4. The kit of claim 1, wherein the coating solution comprises from about 0.01 to about 20 weight percent of the wetting agent.

5. The kit of claim 1, wherein the coated non-hydrated pre-formed cross-linked gelatin pledget comprises from about 0.01 to about 5 weight percent of the wetting agent.

6. The kit of claim 5, wherein the coated non-hydrated pre-formed cross-linked gelatin pledget is bioabsorbable.

* * * * *